(12) United States Patent
Clark, Jr. et al.

(10) Patent No.: US 8,403,903 B2
(45) Date of Patent: Mar. 26, 2013

(54) INDIVIDUAL, EXPANDABLE WRAPPER FOR A HYGIENE PRODUCT

(75) Inventors: James Joseph Clark, Jr., Appleton, WI (US); Garry Roland Woltman, Appleton, WI (US); Susan Jean Moder, Appleton, WI (US); Annaïg Gaël Jacquemard, Forchheim (DE); Roland Eckehard Nepf, Eckental (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2112 days.

(21) Appl. No.: 11/214,401

(22) Filed: Aug. 29, 2005

(65) Prior Publication Data

US 2007/0049891 A1    Mar. 1, 2007

(51) Int. Cl.
*A61F 13/15* (2006.01)
*A61L 15/00* (2006.01)

(52) U.S. Cl. ......... 604/385.02; 604/385.06; 604/385.13; 604/385.19; 206/440; 206/438

(58) Field of Classification Search ............. 604/385.02, 604/385.06, 385.13, 385.19; 206/440, 438
See application file for complete search history.

(56) References Cited

U.S. PATENT DOCUMENTS

| | | | |
|---|---|---|---|
| 3,230,956 A | 1/1966 | Kargul | |
| 3,274,999 A | 9/1966 | Robinson | |
| 3,369,545 A | 2/1968 | Wanberg | |
| 3,604,423 A * | 9/1971 | Fraser | 604/385.13 |
| 3,620,217 A | 11/1971 | Gellert | |
| 3,731,689 A | 5/1973 | Schaar | |
| 3,865,110 A | 2/1975 | Traverse | |
| 3,877,432 A | 4/1975 | Gellert | |
| 3,920,019 A | 11/1975 | Schaar | |
| 3,927,674 A | 12/1975 | Schaar | |
| 3,973,567 A | 8/1976 | Srinivasan et al. | |
| 4,034,760 A | 7/1977 | Amirsakis | |
| 4,085,753 A | 4/1978 | Gellert | |
| 4,182,336 A * | 1/1980 | Black | 604/385.13 |
| 4,186,743 A | 2/1980 | Steiger | |
| 4,336,804 A | 6/1982 | Roeder | |

(Continued)

FOREIGN PATENT DOCUMENTS

EP    0 496 716 A1    7/1992
EP    0 374 730 B2    4/1994

(Continued)

*Primary Examiner* — Jacqueline F. Stephens
(74) *Attorney, Agent, or Firm* — Randall W. Fieldhack

(57) ABSTRACT

An article (20) has a longitudinal length (22), an article width (24) and an article thickness (26). The article (20) comprises a fresh personal care product (28) in a substantially unsoiled condition, and a pouch (30) having a pouch volume which operatively encloses the fresh product (28). The pouch (30) includes a front panel region (32), a back panel region (34) which is operatively connected to the front panel region (32), and at least one expansion section (48) which is operatively connected between the front panel region (32) and the back panel region (34). The expansion section (48) is operatively held in a substantially unexpanded, closed position when the fresh product (28) is enclosed in the pouch (30). The expansion section 48 is movable to an open position after a removal of the fresh product (28) from the pouch (30). The open position of the expansion section (48) is configured to provide an expanded disposal volume which can operatively contain a product (28) when the product (28) is in a used and soiled condition.

15 Claims, 8 Drawing Sheets

U.S. PATENT DOCUMENTS

| | | |
|---|---|---|
| 4,337,772 A | 7/1982 | Roeder |
| 4,376,440 A | 3/1983 | Whitehead et al. |
| 4,376,772 A | 3/1983 | Saari et al. |
| 4,380,450 A | 4/1983 | Reich |
| 4,430,087 A | 2/1984 | Azpiri |
| 4,475,913 A | 10/1984 | Hlaban |
| 4,493,713 A * | 1/1985 | Izzo .................. 604/385.13 |
| 4,551,145 A | 11/1985 | Ryan |
| 4,581,027 A | 4/1986 | Alvarado |
| 4,604,096 A | 8/1986 | Dean et al. |
| 4,605,403 A | 8/1986 | Tucker |
| 4,631,062 A | 12/1986 | Lassen et al. |
| 4,692,162 A | 9/1987 | Binker et al. |
| 4,735,316 A | 4/1988 | Froidh et al. |
| 4,772,282 A | 9/1988 | Oakley |
| 4,781,712 A | 11/1988 | Barabino et al. |
| 4,808,175 A | 2/1989 | Hansen |
| 4,838,327 A | 6/1989 | Ambler et al. |
| 4,846,828 A | 7/1989 | Mendelsohn |
| 4,857,066 A | 8/1989 | Allison |
| 4,869,724 A | 9/1989 | Scripps |
| 4,923,455 A | 5/1990 | Dean et al. |
| 4,931,052 A | 6/1990 | Feldman |
| 4,959,265 A | 9/1990 | Wood et al. |
| 4,964,859 A | 10/1990 | Feldman |
| 4,968,311 A | 11/1990 | Chickering et al. |
| 5,019,065 A | 5/1991 | Scripps |
| 5,108,384 A | 4/1992 | Goulait |
| 5,141,505 A | 8/1992 | Barrett |
| 5,149,335 A | 9/1992 | Kellenberger et al. |
| 5,176,671 A | 1/1993 | Roessler et al. |
| 5,259,503 A | 11/1993 | Steingraber, Jr. |
| 5,279,604 A | 1/1994 | Robertson et al. |
| 5,287,960 A | 2/1994 | Kalb et al. |
| 5,304,158 A | 4/1994 | Webb |
| 5,358,499 A | 10/1994 | Seidy |
| 5,387,450 A | 2/1995 | Stewart |
| 5,403,302 A | 4/1995 | Roessler et al. |
| 5,404,999 A | 4/1995 | Bednar |
| 5,429,630 A | 7/1995 | Beal et al. |
| 5,478,336 A | 12/1995 | Pigneul |
| 5,569,230 A | 10/1996 | Fisher et al. |
| 5,575,784 A | 11/1996 | Ames-Ooten et al. |
| 5,579,916 A | 12/1996 | Manko |
| 5,582,605 A | 12/1996 | Lepie |
| 5,611,789 A | 3/1997 | Seth |
| 5,611,790 A | 3/1997 | Osborn, III et al. |
| 5,662,758 A | 9/1997 | Hamilton et al. |
| D386,582 S | 11/1997 | Levine |
| 5,688,258 A | 11/1997 | Rawat et al. |
| 5,702,379 A | 12/1997 | Preiss |
| 5,706,950 A | 1/1998 | Houghton et al. |
| D393,713 S | 4/1998 | Gubbiotti |
| 5,778,110 A | 7/1998 | Furuya |
| 5,797,896 A | 8/1998 | Schmitz |
| 5,833,646 A | 11/1998 | Masini |
| H1788 H | 2/1999 | Christon et al. |
| 6,007,527 A | 12/1999 | Kawaguchi et al. |
| 6,059,100 A | 5/2000 | Jones |
| 6,120,743 A | 9/2000 | Papari |
| 6,210,386 B1 | 4/2001 | Inoue |
| 6,264,644 B1 | 7/2001 | Igaue et al. |
| D448,479 S | 9/2001 | Foy |
| 6,451,000 B1 | 9/2002 | Hayase et al. |
| 6,454,748 B1 | 9/2002 | Ives |
| 6,544,242 B1 | 4/2003 | Kido et al. |
| 6,572,600 B1 | 6/2003 | Roe et al. |
| 6,599,262 B1 | 7/2003 | Masini |
| 6,623,466 B1 | 9/2003 | Richardson |
| 6,664,435 B2 | 12/2003 | Masini |
| 6,702,116 B2 | 3/2004 | Hummel |
| D494,852 S | 8/2004 | Meador et al. |
| 2001/0003152 A1 | 6/2001 | Lee |
| 2002/0056655 A1 | 5/2002 | Cottingham et al. |
| 2002/0060167 A1 | 5/2002 | Nichols et al. |
| 2002/0063076 A1 | 5/2002 | Kolterjohn et al. |
| 2002/0078665 A1 | 6/2002 | Salman et al. |
| 2002/0079246 A1 | 6/2002 | Ling et al. |
| 2002/0084203 A1 | 7/2002 | Cottingham et al. |
| 2002/0153271 A1 | 10/2002 | Mcmanus et al. |
| 2002/0170275 A1 | 11/2002 | Salman et al. |
| 2002/0178482 A1 | 12/2002 | Samuelsson et al. |
| 2003/0023217 A1 | 1/2003 | Mcmanus et al. |
| 2003/0073970 A1 | 4/2003 | Suga |
| 2003/0078552 A1 | 4/2003 | Tepper et al. |
| 2003/0153891 A1 | 8/2003 | Molee |
| 2003/0199842 A1 | 10/2003 | Luizzi et al. |
| 2004/0266302 A1 | 12/2004 | Disalvo et al. |

FOREIGN PATENT DOCUMENTS

| | | |
|---|---|---|
| EP | 0 684 029 A2 | 11/1995 |
| EP | 0 841 049 A1 | 5/1998 |
| EP | 1 043 004 A2 | 10/2000 |
| EP | 1 062 931 A1 | 12/2000 |
| FR | 2 638 426 A1 | 5/1990 |
| GB | 2 060 398 | 5/1981 |
| GB | 2 302 026 A | 1/1997 |
| GB | 2 326 811 A | 1/1999 |
| GB | 2 354 171 A | 3/2001 |
| GB | 2 354 172 A | 3/2001 |
| GB | 2 386 108 A | 9/2003 |
| GB | 2 407 307 A | 4/2005 |
| WO | WO 96/27354 A1 | 9/1996 |
| WO | WO 01/89947 A1 | 11/2001 |
| WO | WO 2004/010914 A1 | 2/2004 |
| WO | WO 2004/021948 A1 | 3/2004 |

* cited by examiner

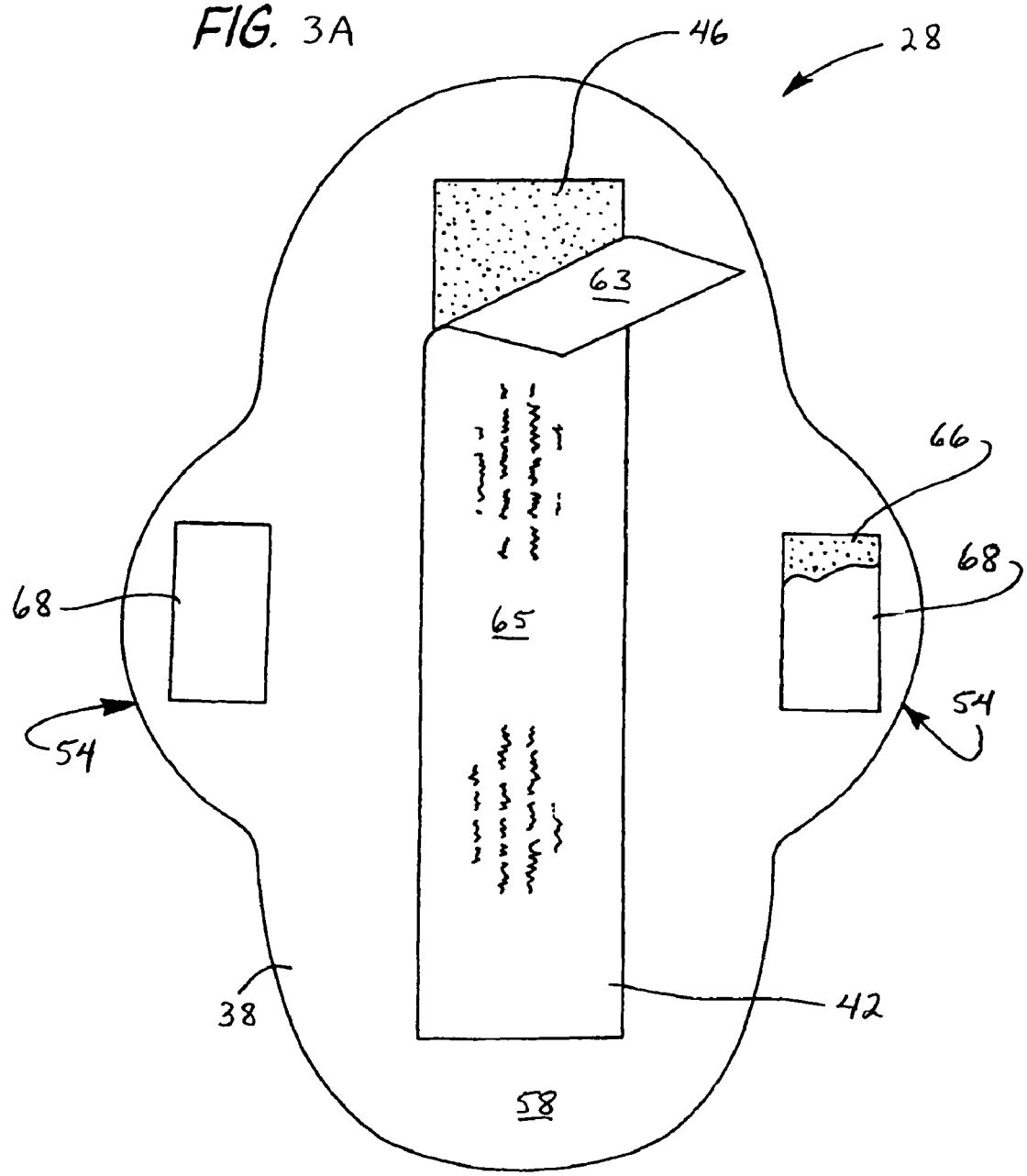

INDIVIDUAL, EXPANDABLE WRAPPER FOR A HYGIENE PRODUCT

BACKGROUND OF THE INVENTION

The present invention relates generally to personal care products and more particularly to a product configuration which can more effectively wrap the product and provide for a more convenient disposal of the product after the product has been soiled.

The personal care products can, for example, be absorbent products, and such products may be adult incontinence products and feminine care products, such as panty liners and feminine napkins and the like. The individual products may have areas coated with adhesive materials for attaching the product to a crotch area of clothing to hold the product in place adjacent a wearer's body during use. Typically, a label or covering layer has been removably attached to the adhesive coating to cover the coating and to prevent attachment of the product before the user removes the covering from the adhesive coating.

The individual personal care products have also been wrapped or otherwise enclosed in individual wrappers or pouches. Additionally, desired groupings of the personal care products have been packaged using conventional techniques and outer containers, such as bags, boxes, cartons and the like.

The individual wrappers and pouches have often been used to hold the products after the products have been used and soiled. To further assist in the disposal of soiled products, the individual personal care products have been configured to include supplemental disposal bags that have been attached to or assembled with the individual products.

Conventional wrappers, pouches and disposal bags, such as those described above, have had various shortcomings. Typically, the soiled product has increased in size due to its ordinary use and the associated absorption of liquids. Consequently, the originally provided wrappers, pouches and bags have not been sufficiently large to readily enclose and contain the product in its larger, soiled condition. Conventional wrappers, pouches and disposal bags have also not provided sufficient visual masking of the contained product, and have not provided sufficient control or masking of malodor. As a result, there has been a continued need for improved individual wrapping systems and configurations that can more effectively hold an individual, soiled product for convenient and discreet disposal.

SUMMARY OF THE INVENTION

The present invention can provide an article which comprises a fresh personal care product in a substantially unsoiled condition, and a pouch having a pouch volume which operatively encloses the fresh product. The pouch can include a front panel region, a back panel region which is operatively connected to the front panel region, and at least one expansion section which is operatively connected between the front panel region and the back panel region. The expansion section can be operatively held in a substantially unexpanded, closed position when the fresh product is enclosed in the pouch, and the expansion section can be movable to an open position after a removal of the fresh product from the pouch. The open position of the expansion section can be configured to provide an expanded disposal volume which can operatively contain a product when the product is in a used and soiled condition.

By incorporating its various aspects and features, the method of the present invention can provide an improved and more effective system for readily enclosing and containing the product in its relatively larger size, after the product has absorbed a significant amount of liquid. The present invention can also provide an improved visual masking of the contained product, and can provide an improved control or masking of malodor. As a result, the arrangements of the present invention can provide individual wrapping systems and configurations that can more effectively hold an individual, soiled product for convenient and discreet disposal.

BRIEF DESCRIPTION OF THE DRAWINGS

The invention will be more fully understood and further advantages will become apparent when reference is made to the following detailed description of the invention and to the drawings in which:

FIG. 3A shows a representative, plan view of a garment-side of a representative product that can be employed with the present invention.

Corresponding reference characters indicate corresponding parts throughout the several views of the drawings.

DETAILED DESCRIPTION OF THE INVENTION

Figure 1:
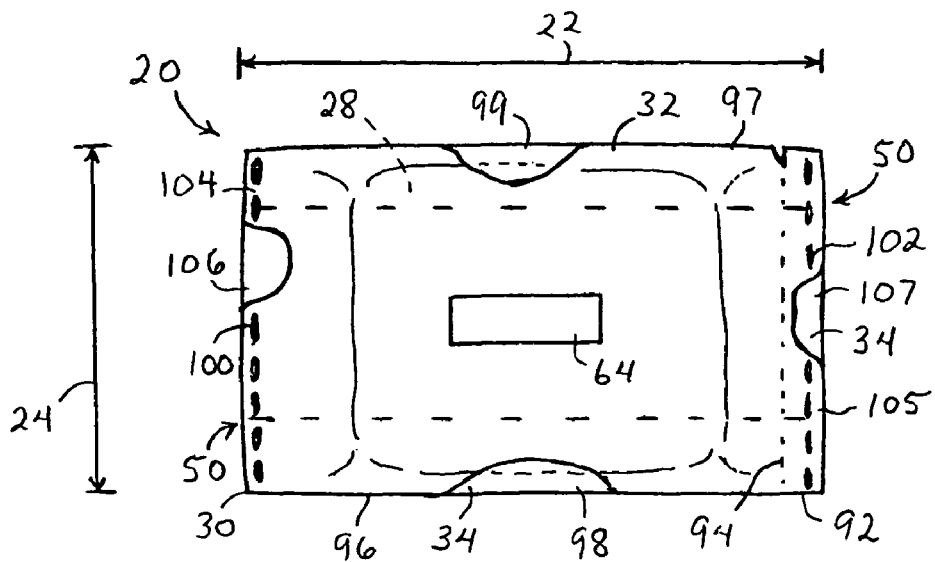
FIG. 1 shows a partially cut-away, plan view of a representative article of the invention.
Figure 1A:
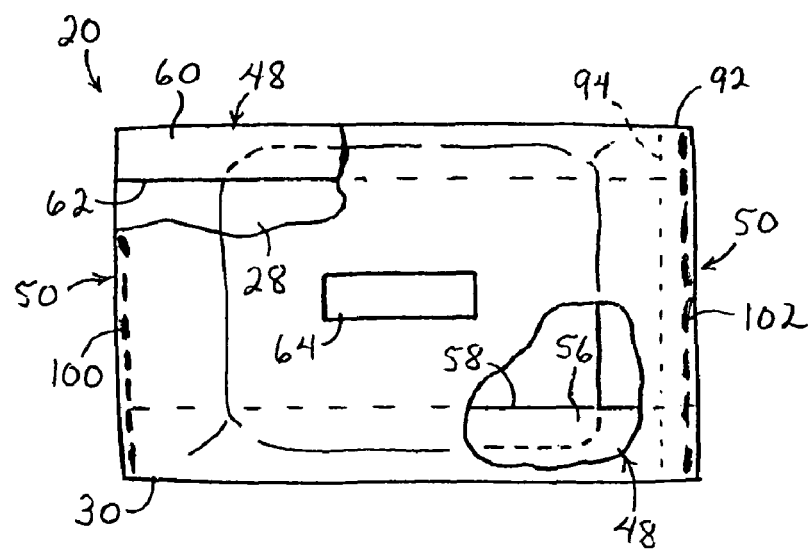
FIG. 1A shows another, partially cut-away, plan view of a representative article of the invention.
Figure 2:
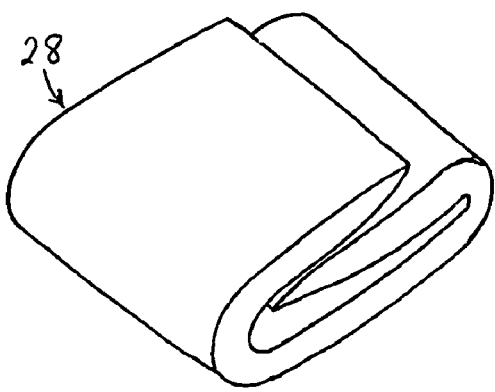
FIG. 2 shows a representative product that has been folded for use with the present invention.

When introducing elements of the present disclosure, the products "a", "an", "the" and "said" are intended to mean that there are one or more of the elements. The terms "comprising", "including" and "having" are intended to be inclusive and mean that there may be additional elements other than the listed elements. Such terms are intended to be open-ended terms that specify the presence of any stated features, elements, integers, steps, or components, and are not intended to preclude the presence or addition of one or more other features, elements, integers, steps, components, or groups thereof.

As representatively shown in FIGS. 1-2, FIGS. 5-5B and FIGS. 6-6A, an article 20 has a longitudinal, article length 22, and an article width 24. Additionally, the article has an article thickness that is perpendicular to the article length and article width, and extends into the plane of the drawing in FIG. 1. The article 20 comprises a personal care product 28 in a fresh, substantially unsoiled condition, and a pouch 30 having a pouch volume which operatively encloses the fresh product 28. The pouch 30 can include a front panel region 32, a back panel region 34 which is operatively connected to the front panel region 32, and at least one expansion section 48 which is operatively connected between the front panel region 32 and the back panel region 34. The expansion section 48 can be operatively held in a substantially unexpanded, closed position when the fresh product 28 is enclosed in the pouch 30. The expansion section 48 can be movable to an open position after a removal of the fresh product 28 from the pouch 30. The open position of the expansion section 48 can be configured to provide an expanded disposal volume which can operatively contain a product 28 when the product 28 is in a used and soiled condition.

The article 20 can further include a pouch closure mechanism 50 which operatively holds the pouch 30 in a closed configuration that suitably encloses the fresh product 28. Additionally, the article can include a pouch-opening mechanism 92 that can operatively allow a removal of the fresh product 28 from the pouch 30. After the pouch has been opened and expanded, the opened pouch can be configured to provide a disposal volume that is significantly larger than the initial volume of the pouch when the pouch was arranged to hold the fresh product. The disposal volume of the expanded pouch can be readily configured to provide dimensions and size that are sufficient to contain the soiled product for convenient disposal. Additionally, the article may include a containment-closure mechanism 64 which is configured to hold a pouch 30 in an expanded and closed disposal condition which contains the soiled product.

By incorporating its various aspects and features, the article of the present invention can provide an improved and more effective system for readily enclosing and containing the product in the relatively larger size that occurs after the product has absorbed a significant amount of liquid. The present invention can also provide a more effective system for visually masking the contained product. In another feature, the invention can provide an improved system for controlling or masking malodor. As a result, the arrangements of the present invention can provide individual wrapping systems and configurations that can more effectively hold an individual, soiled product for convenient and discreet disposal. Additionally, the present invention can provide a more sanitary arrangement during the disposal of the soiled article. Such arrangements can help limit the exposure of the soiled product to the surrounding environment. As a result, any potential of contamination of the surrounding environment can be reduced.

In a particular configuration of the invention, the products 28 can be personal care products, and in a further configuration, the products can be absorbent products. Additionally, the products may be disposable. As used herein, the term "absorbent product" refers to devices which can absorb and contain body liquids, and more specifically, refers to devices which are placed against or near the skin to absorb and contain the various liquids discharged from the body. The term "disposable" is used herein to describe absorbent products that are not intended to be laundered or otherwise restored or reused as an absorbent product after a single use. Examples of such disposable absorbent products include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats. In desired arrangements, the method of the invention can be employed with feminine care products.

Figure 3:
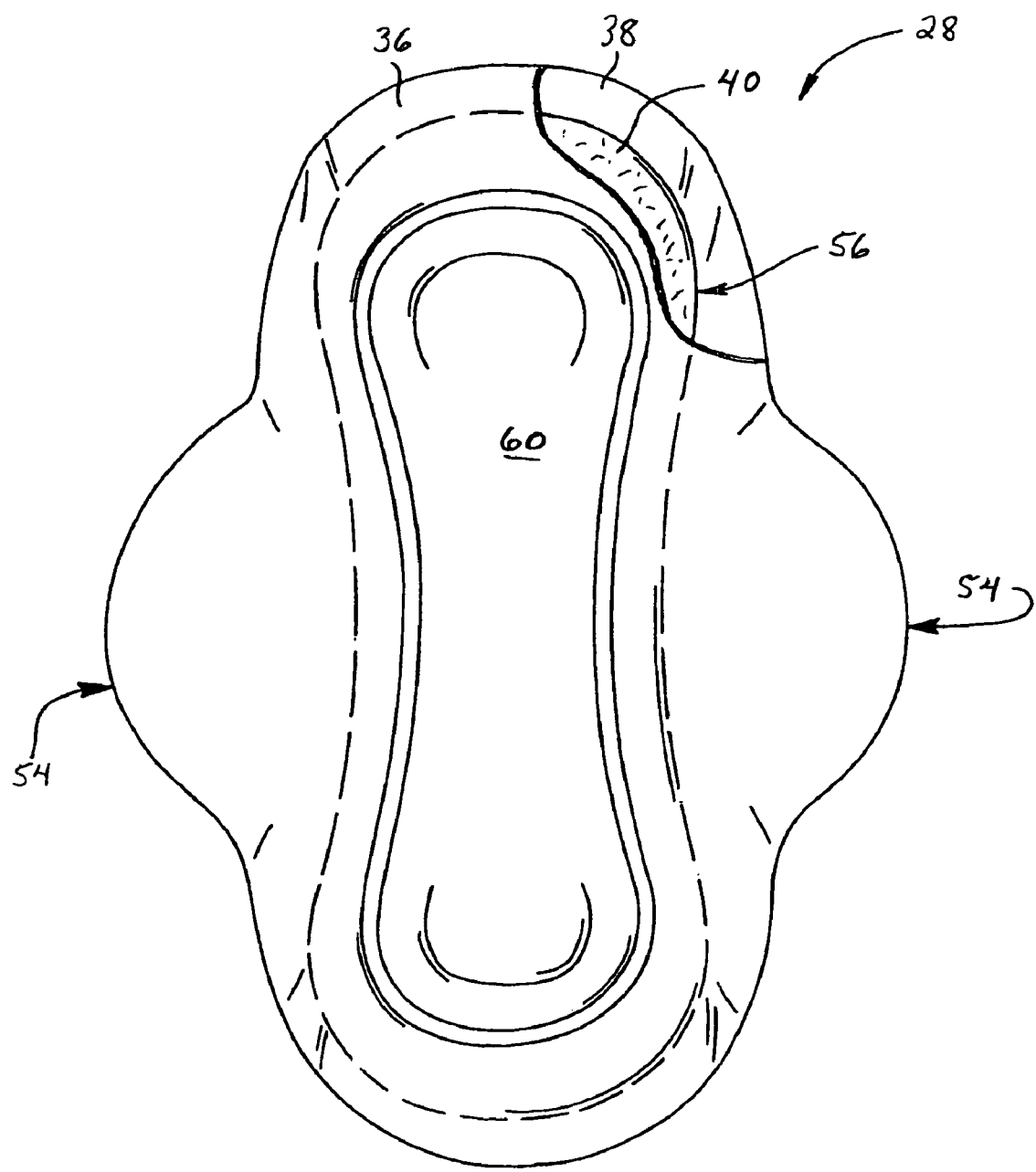
FIG. 3 shows a representative, plan view of a bodyside of a representative product that can be employed with the present invention.

Referring now to the drawings and in particular to FIGS. 3 and 3A, a representative product is designated in its entirety by the reference numeral 28. Although the shown example product 28 is an absorbent feminine napkin, those skilled in the art will appreciate that the present invention may be employed with other feminine care products, such as panty liners, as well as other personal care absorbent products, such as adult care incontinence products, child care products and infant care products.

With reference to FIGS. 3 and 3A, the personal care product 28 can have a laminated structure which includes a liquid-permeable topsheet layer 36, and a backsheet layer 38. In particular aspects, the product can further include an absorbent body 40 that is positioned and held between the topsheet layer and backsheet layer. The topsheet layer 36 can comprise any operative, liquid-permeable material. For example, the topsheet layer can include a polymer film, a woven fabric, a nonwoven fabric or the like, as well as combinations thereof. The employed polymer films may be porous, or may be treated or otherwise processed to impart the desired level of liquid-permeability.

The backsheet layer 38 can comprise a polymer film, a woven fabric, a nonwoven fabric or the like, as well as combinations thereof. In desired arrangements, the backsheet layer 38, can be configured to be operatively liquid-impermeable, and can sufficiently block the movement of body-liquids through the thickness of the backsheet layer during ordinary use. In another feature, the backsheet layer 38 can be configured to be gas-permeable or "breathable". Such breathable backsheet layer materials are well known and available from commercial vendors.

The product 28 may or may not include the absorbent body 40. When present in the product, the absorbent body 40 can include any operative absorbent material. Examples of suitable absorbent materials can include natural fibers, synthetic fibers, woodpulp fibers, cellulosic fibers, synthetic polymer fibers, thermoplastic binder fibers, bicomponent binder fibers or the like, as well as combinations thereof. Additionally, the absorbent body 40 can include superabsorbent materials which can typically absorb and retain large amounts of aqueous liquids per unit weight of the superabsorbent material. The superabsorbent materials have very high absorbent capacities and swell to form hydrogels that are substantially water-insoluble. Such superabsorbent materials are well known and are readily available from commercial vendors.

The absorbent body 40 and/or its corresponding product 28 can be configured to provide any operative level of absorbent saturation capacity (saturation retention capacity). Typically, the absorbent capacity pertains to the ability to absorb and hold liquids, such as water, saline, urine, synthetic urine, menses or menses simulant, or the like. Particular arrangements of an adult incontinence product can be configured to provide an absorbent saturation retention capacity which is at least a minimum of about 100 grams or 150 grams of urine simulant. The absorbent saturation capacity can alternatively be at least about 200 grams of urine simulant, and can optionally be at least about 300 grams of urine simulant to provide improved benefits. In other aspects, the product and/or its absorbent body can have a saturation capacity of up to about 1000 grams of urine simulant, or more. In a feminine care product, the absorbent saturation capacity can be a minimum of about 0.1 grams of menses simulant, or less. In other aspects, the saturation capacity can be up to a maximum of about 100 grams of menses simulant.

A suitable urine simulant for determining absorbent capacity is 0.9 wt % saline (solution composed of water and 0.9 wt % NaCl). A suitable menses simulant is composed of swine blood diluted with swine plasma to provide a hematocrit level of 35%, (by volume). A suitable device for determining the hematocrit level is a HEMATOSTAT-2 system, available from Separation Technology, Inc., a business having offices located in Altamonte Springs, Fla., U.S.A. Alternatively, a substantially equivalent device or system may be employed.

The absorbent body has a peripheral edge 56. Additionally, the product 28 can have a first, garment-facing side, and a second, bodyside that is located opposite the garment-side. Tabs or side-panels, generally designated by 54, may be incorporated, and an individual side-panel can be configured to extend laterally from each lateral edge of the absorbent body 40 for wrapping around the crotch of the user's underwear (not shown) to protect it from staining. The tabs may also be referred to as "wings". As illustrated, each side-panel 54 may include a tab fastener, such as provided by the representatively shown adhesive strip 66 or other adhesive region, for attaching either or both side-panels in a conventional manner to an outside surface of a crotch section of the user's underwear to hold the side-panels 54 of the personal care product 28 in place around the underwear during use. The adhesive strips 66 may be covered with a removable peel strip member 68 to prevent the adhesive strips from sticking to other surfaces until ready for use.

As further illustrated, a garment-attachment mechanism, such as provided by the representatively shown region of garment adhesive 46, can be also applied to the garment side of the product, thereby permitting a user to attach the product to a preselected surface, such as the inside surface of the crotch of the user's underwear, to hold the personal care product 28 in place on the underwear during use. As representatively shown, the garment-attachment mechanism can include a coating or other distributed pattern of adhesive 46 (e.g., a two-sided adhesive film or tape). The garment adhesive can be disposed on the garment-side of the backsheet 38, and can be configured to provide an operative garment-fastener. Accordingly, each individual product can include a garment adhesive layer that is secured to an outward, garment-facing surface of the corresponding backsheet layer 38 of the individual product. The removable layer 42 of each product 28 can be removably secured to the garment-adhesive layer or other garment-attachment mechanism of each product 28. Although the adhesive garment-fastener 46 may have other sizes and shapes without departing from the scope of the present invention, in one embodiment the adhesive coating can be generally rectangular and can have a width of about three centimeters and a length of about 17 centimeters.

A label or other removable layer 42 can be removably attached to the garment-attachment mechanism. For example, the removable layer can be removably joined to the adhesive fastener 46 to prevent attachment of the absorbent body 40 before the user removes the covering, removable layer from the adhesive coating. Although the removable layer 42 may have other sizes and shapes without departing from the scope of the present invention, in one embodiment the removable layer can have a size and shape selected for entirely covering the adhesive fastener 46 when attached to the adhesive coating. More particularly, in one embodiment the removable layer 42 can be rectangular and can have a width of about four centimeters and a length of about 18 centimeters. Because the removable layer 42 can be longer and/or wider than the adhesive fastener 46, the removable layer can present a loose margin which can be grasped easily by the user when removing the covering, removable layer 42 from the garment-fastener adhesive 46.

It should be readily appreciated that the selected tab fastener (e.g. adhesive fastener 66) and/or the selected garment-attachment fastener (e.g. adhesive fastener 46) can be provided by any operative fastening device or system. For example, the fastener mechanism or system can include an adhesive, a cohesive, an interengaging mechanical fastener, a cooperative component of a hook-and-loop fastener, a magnetic fastener, an electrostatic fastener or the like, as well as combinations thereof.

As illustrated, the garment-attachment fastener can be an operative garment-adhesive, and the removable layer 42 can have a release side 63 for contacting the adhesive fastener 46 when the removable layer is attached to the adhesive. Additionally, the removable layer 42 can have an outward-facing side 65 positioned opposite the release side.

An optional arrangement can include a wing peel-strip layer which is provided by a layer of the material employed to form the tabs or side flap "wings" 54. In a particular aspect, the tabs can have a storage position in which at least one, and desirably both, of the tabs 54 are positioned against the outward-facing, garment-side surface of the backsheet layer 38. For example, either or both of the wing tabs 54 may be folded and positioned generally adjacent and against the outward garment-facing surface of the backsheet layer 38 to provide the desired storage position. From its storage position, the tab is intended to be moved or otherwise repositioned prior to using the product, to enable full functionality of the product. In particular, the tabs can be moved and extended to laterally outboard positions to allow a positioning and securing of the tabs around the lateral side edges of the crotch region of the user's undergarment. Thus, the product can be located and operatively reconfigured in the undergarment prior to using the product, and the reconfigured product will allow a desired, full functionality.

It should be readily appreciated that the personal care product 28 can include various conventional structures, and such structures are well known by those skilled in the art. Thus, the materials used in making the personal care product 28 described above, the detailed construction of the personal care product, and the method of manufacturing the personal care product are well known and will not be described in further detail. Examples of conventional personal care products 28 are described in U.S. Pat. No. 5,429,630, issued Jul. 4, 1995.

The personal care product 28 desirably has a folded configuration when held in its corresponding, individual pouch 30. In a particular aspect, the personal care product 28 has been separately folded prior to engagement with the pouch 30. Accordingly, the pouch 30 can be a component that is provided additional to and separate from the removable layer 42. As representatively shown, for example, the product 28 can be folded into two or more sections, and can desirably be folded into three sections. It should be readily appreciated, however, that the product 28 may be individually folded and placed in its corresponding pouch 30 with any number of folds, and any operative folding pattern or folding sequence without departing from the scope of the present invention.

In the various configurations of the invention, the pouch 30 can operatively include a front panel region 32, and a back panel region 34 which is operatively connected to the front panel region 32. For example, the pouch can include at least two layers of pouch material that are cooperatively connected along a portion of their peripheral edges. The front panel region and/or back panel region may, for example, incorporate a plurality of two or more, separately provided pieces of material that are joined or otherwise operatively connected together. Alternatively, the front panel region and back panel region may be integrally formed from a unitary piece of material. For example, the front panel and back panel regions may be integrally formed from a unitary piece of material that has been folded or otherwise turned over onto itself along an appointed folding or turning region. In still another alternative configuration, the front panel and back panel regions may be provided by a substantially unitary, tube-like arrangement of pouch material that can be sealed or otherwise closed at either or both of its end regions to thereby form the desired pouch.

The article 20 can further include a pouch closure mechanism 50 which can operatively hold the pouch 30 in a closed configuration which envelops or otherwise encloses the fresh product 28. Additionally, the pouch closure mechanism 50 may be configured to help hold the expansion section 48 in a substantially unexpanded, closed position when the fresh product 28 is enclosed in the pouch 30. Any operative, pouch closure mechanism may be employed. For example, the pouch closure mechanism can include an adhesive bond, a cohesive bond, a thermal bond, an ultrasonic bond, a snap fastener, a button fastener, a zipper, a drawstring system, an interengaging mechanical fastener, hook-and-loop fastener or the like, as well as combinations thereof. Additionally, the closure mechanism may have multiple components or sections, and the sections may be distributed in any operative pattern or array (e.g. FIGS. 6 and 6A).

With reference to FIGS. 1-1A and FIGS. 4-4B, the pouch closure mechanism 50 can, for example, include a first side attachment 100 between a first side edge portion 104 of the front panel 32 and a first side edge portion 106 of the back panel 34. The pouch closure mechanism 50 can additionally include a second attachment 102 between a second side edge portion 105 of the front panel region 32 and a second side edge portion 107 of the back panel region 34. The first side attachment 100 between the first side edge portion 104 of the front panel region 32 and the first side edge portion 106 of the back panel region 34 can, for example, be a first bonded attachment. Similarly, the second side attachment 102 between the second side edge portion 105 of the front panel region 32 and the second side edge portion 107 of the back panel region 34 can be a second bonded attachment.

At least one expansion section 48 can be operatively connected between the front panel region 32 and the back panel region 34. The expansion section 48 can include a first gusset member 56 which is operatively interconnected between a first end edge portion 96 of the front panel 32 and a first end edge portion 98 of the back panel 34. The first gusset member can be configured to be expandable in any operative manner. As representatively shown, for example, the first gusset member 56 may have at least one longitudinal fold-line 58 therein. Optionally, the first gusset member 56 can have a selected plurality of longitudinal fold-lines therein.

The expansion section 48 may further include an additional, second gusset member 60 that is operatively interconnected between a second end edge portion 97 of the front panel region 32 and a second end edge portion 99 of the back panel region 34. The second gusset member can be configured to be expandable in any operative manner. As representatively shown, the second gusset member 60 may have at least one longitudinal fold-line 62 therein, and may optionally have a selected plurality of longitudinal fold-lines. Accordingly, a selected gusset member (56, 60) may be configured to have a generally U shape, V shape, multiple-U shape, multiple-V shape, W shape, accordion shape or the like, as well as combinations thereof.

Each gusset member 56, 60 can be integrally formed with at least one of the front panel region 32 and back panel region 34. Alternatively, either or both of the gusset members can be a separately provided component or member. The gusset member can be constructed with any operative material, and the material may be elastomeric, non-elastomeric, extensible, non-extensible, stretchable, non-stretchable or the like, as well as combinations thereof. For example, the material of the gusset member may include a polymer film, a woven fabric, a nonwoven fabric, a fabric-film laminate, paper, cellulosic tissue or the like, as well as combinations thereof.

In the various configurations of the invention, the appointed expansion member 48 can be operatively held in a substantially unexpanded, closed position when the fresh product 28 is enclosed in the pouch 30. For example, at least one of the first gusset member 56 and the second gusset member 60 can be operatively held in a substantially unexpanded, folded, closed position when the fresh product 28 is enclosed in the pouch 30. Desirably, both of the gusset members can be operatively held in a substantially unexpanded, folded, closed position when the fresh product 28 is enclosed in the pouch.

Any operative holding mechanism may be employed to operatively maintain the expansion section 48 in the desired, substantially unexpanded, closed position. For example, the holding mechanism can include an adhesive bond, a cohesive bond, a thermal bond, an ultrasonic bond, a snap fastener, a button fastener, a zipper, an interengaging mechanical fastener, hook-and-loop fastener or the like, as well as combinations thereof. The holding mechanism may be arranged in any operative distribution pattern, and the distribution pattern may be irregular, substantially regular, discontinuous or substantially continuous, as well as combinations of discontinuous and continuous portions.

As representatively shown, for example, the holding mechanism can include the first side attachment 100 between the first side edge portion 104 of the front panel 32 and the first side edge portion 106 of the back panel 34. The holding mechanism can additionally include the second attachment 102 between the second side edge portion 105 of the front panel region 32 and the second side edge portion 107 of the back panel region 34.

The article 20 can additionally include a pouch-opening mechanism 92 which can operatively allow a removal of the fresh product 28 from the pouch 30. For example, the pouch opening mechanism 92 can include an appointed line of frangibility 94 or other line of separability which can be positioned to extend along a selected side attachment (e.g. side attachment 102). For example, the appointed line of separability or frangibility 94 can be located generally adjacent to and relatively inboard from the first side attachment 100.

With the various configurations of the invention, any operative technique or mechanism can be employed to provide the desired frangibility or other separability. The appointed line of separability may, for example, be provided by any operative weakening mechanism. A suitable weakening mechanism may include a chemical weakening, a thermal weakening, a mechanical weakening, a line or pattern of weakening embossments, a predetermined line or pattern of discontinuities that will operatively induce high stress concentrations upon the application of an applied opening force, or the like, as well as combinations thereof. As representatively shown, the appointed line of frangibility 94 can include a line of perforations that extends an operative distance along the width direction 24 of the pouch 30. Alternatively, the frangibility or other separability can be provided by a releasable bond, a releasable fastener, a releasable adhesive, a low-strength bond, a low-strength adhesive, a low-strength fastener, a releasable latching mechanism, a zipper mechanism, a tear strip or the like, as well as by any operative combination of the frangibility or separability techniques or mechanisms that are disclosed herein.

The line of frangibility 94 can be visually or tactilely highlighted to facilitate the finding and use of the frangibility line. The highlighting may, for example, include a printing or other application of a set of dashes or other operative indicia along the line of frangibility, and the selected indicia can have a color that significantly contrasts with the predominate color of the pouch. Another example of the highlighting can include a notch provided on the edge of the pouch where the line of frangibility intersects the outer perimeter of the pouch. Additionally, the pouch may include written instructions regarding the use of the line of frangibility. For example, the pouch may include an instructional label, such as a label which states, "Tear here to open."

Figure 4:
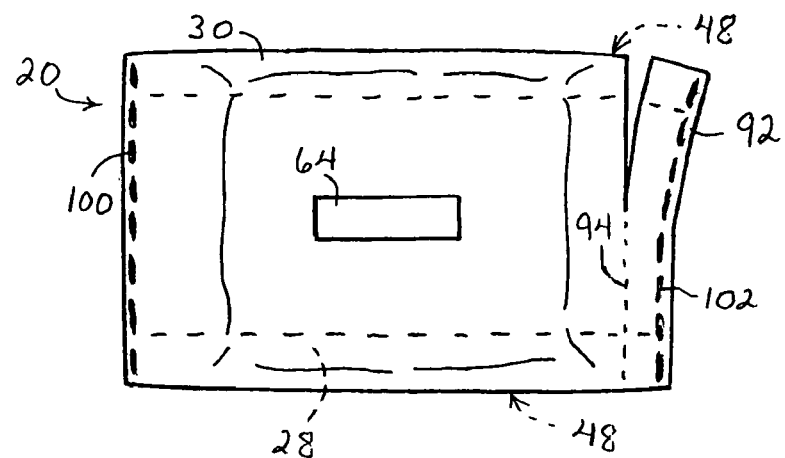
FIG. 4 shows another representative article of the invention wherein an opening mechanism is being activated to allow access to the enclosed product.
Figure 4A:
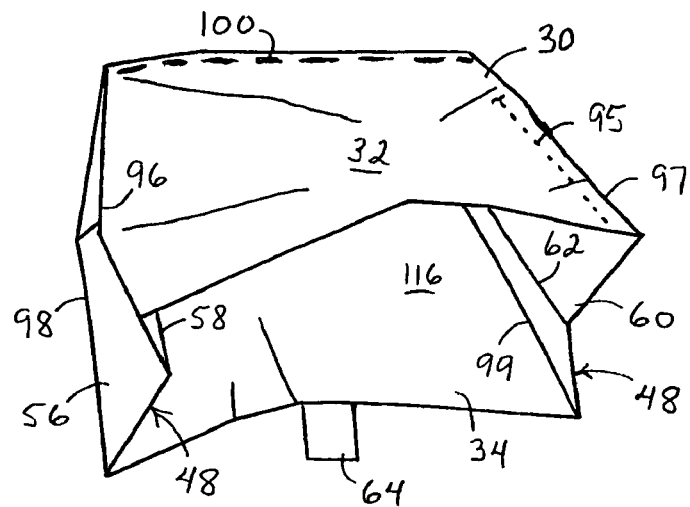
FIG. 4A shows a representative article of the invention which has been configured to provide an opened and expanded pouch.
Figure 4B:
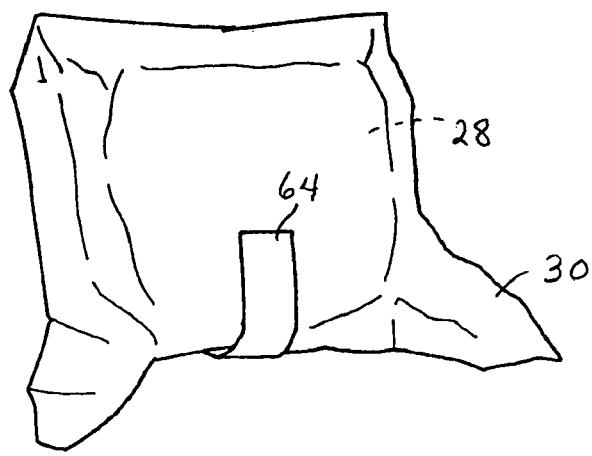
FIG. 4B shows a representative expanded pouch which has been closed to contain a soiled product.

During or after the opening of the pouch, a sufficient portion of the holding mechanism, which maintains the expansion section 48 in its closed position, can be operatively deactivated or overridden. With reference to FIGS. 4 and 4A, for example, the pouch can be torn or otherwise opened along the appointed line of frangibility. The tearing or other opening action can effectively remove the holding operation provided by at least one of the side attachments 100, 102. The tearing or other opening action can effectively deactivate a sufficient portion of the holding mechanism to allow an operative opening of the expansion section.

After the pouch 30 has been opened and the fresh product 28 has been removed from the pouch, the expansion section 48 can be readily movable to the desired open, expanded position. The expanded pouch has an opening 130 that is wide enough to accept a used absorbent article that has been swollen with absorbed liquids. Additionally, the opened position of the expansion section can operatively reconfigure the pouch to provide a disposal container having an increased container volume that is significantly larger than the initial volume of the pouch when the pouch was arranged to hold the fresh product. The resulting container generated by the expanded pouch can have dimensions and size that are sufficient to provide a disposal volume that can operatively contain the product 28 when the product has swollen to a size that significantly exceeds the size of the initial, fresh product. Accordingly, the disposal volume of the container provided by the expanded pouch can have dimensions and size that are sufficient to contain the used and soiled product for convenient disposal.

With reference to FIG. 4A, for example at least one, and desirably both of the gusset members 56, 60 can be movable to an open position after a removal of the product 28 from the pouch 30. The open positions of the first gusset member 56 and second gusset member 60 can be configured to provide an opening that is wide enough to accept a used absorbent article that has been swollen with absorbed liquids. Additionally, the opened positions of the first gusset member 56 and/or second gusset member 60 can provide an expanded container volume which can operatively enclose and hold the product 28 when the product is in its used and soiled condition.

The expanded pouch, container volume is significantly larger than the pouch volume employed to hold the fresh product 28. The product can have an initial volume, as determined under a restraining pressure of 0.1 psi (0.69 KPa), when the product is in its fresh condition. Additionally, the product can have a swollen-volume after the product has absorbed a selected volume of 0.9 wt % saline. In a particular aspect, the container volume of the expanded pouch (e.g. as provided when the expansion section is in its operative, open position) can be configured to be large enough to provide an expanded disposal volume which is can operatively contain the product after the product has absorbed 20% of the total saturated retention capacity of the product (e.g. after the product's corresponding absorbent body absorbed 20% of the total saturated retention capacity of the absorbent body). The container volume can alternatively be large enough to hold the product after the product has absorbed 40% of the product's saturated retention capacity, and can optionally be large enough to hold the product after the product has absorbed 50% of the product's saturated retention capacity. In other aspects, the container volume can alternatively be large enough to hold a product after the product has absorbed 60% or 70% or more of the product's total saturated retention capacity to provide desired benefits.

The saturated retention capacity is a measure of the total absorbent capacity of an absorbent body, absorbent garment, or other absorbent article or product. The saturated retention capacity can be determined as follows. The article or product to be tested, having a moisture content of not more than a maximum of 7 weight percent, is weighed and then submerged in an excess quantity of synthetic urine (0.9 wt % saline) that has been provided at room temperature (about 23° C.). The product is allowed to remain submerged for 20 minutes. After 20 minutes, the product is removed from the saline and placed on a fiberglass screen, which is coated with TEFLON (polytetrafluoroethylene) material, and has 0.25 inch (6.35 mm) screen openings (commercially available from Taconic Plastics Inc. Petersburg, N.Y., U.S.A.). The product and screen are placed on a vacuum box and covered with a flexible rubber dam, sheet product. A vacuum of 3.5 kilopascals (0.5 pounds per square inch) is drawn in the vacuum box for a period of 5 minutes. The product is then weighed. The amount of liquid retained by the product being tested is determined by subtracting the dry weight of the product from the wet weight of the product (after application of the vacuum), and is reported as the saturated retention capacity in grams of liquid retained.

Further details regarding a suitable measurement of the saturated retention capacity of a product or material are disclosed in U.S. Pat. No. 5,149,335 entitled ABSORBENT STRUCTURE by S. Kellenberger et al. which issued Sep. 22, 1992. The entire disclosure of this document is incorporated herein by reference in a manner that is consistent herewith.

The pouch may also include an indicator mechanism which communicates that the pouch has been completely opened. For example, the indicator mechanism can include a visible line which extends at a slanted angle across a gusset fold line on the gusset structure. When the pouch is fully opened and expanded, the indicator line appears straight, and when the pouch is not fully expanded, the indicator line appears bent. Another example of the indicator mechanism may include a circle that extends across a gusset fold line on the gusset structure. When the pouch is fully opened and expanded, the circle appears as a round circle, and when the pouch is not fully expanded, the circle appears flattened.

It may be desirable to increase the size of the opening into the container provided by the expanded pouch. To facilitate placement of the soiled product into the container, a supplemental flap section may be provided on the pouch. The supplemental flap may be created by the user during the use of the pouch. To facilitate the creation of the flap, the pouch can be provided with one or more supplemental lines of frangibility. A particular configuration of the invention can, for example, include the supplemental line of frangibility 95 representatively shown in FIG. 4A. The supplemental line of frangibility can be located generally adjacent or proximate a lengthwise edge of a selected one of the pouch panels 32, 34, or gusset members 58, 60; and can be configured to extend generally along an operative portion of the length dimension 22 of the pouch. For example, the supplemental line of frangibility 95 can be non-perpendicular or substantially perpendicular to the primary line of frangibility 94 of the pouch opening mechanism 92, and can extend between the side attachments 100, 102. Accordingly, the supplemental line of frangibility 95 may be placed on the front panel, back panel, or gusset member, and can have a length which is within the range of about 1% to 100% of the overall length of the pouch. The supplemental line of frangibility may be highlighted to make it easier to locate and utilize. The associated pouch panel can be selectively separated along the supplemental line of frangibility 95 to allow a further opening of the pouch, and provide a larger opening into the expanded pouch. After opening the pouch along the supplemental line frangibility 95, the user can pull back an access flap that has been created. With the access flap pulled back, a significantly larger opening can be created to allow an easier placement of the soiled product into the expanded pouch container. After the soiled product is placed in the expanded container, the access flap can be closed, and the containment closure mechanism 64 can be configured to operatively hold the expanded pouch container in closed condition for disposal.

As representatively shown, the article 20 can further include a containment-closure mechanism 64 which is configured to hold a pouch 30 in an expanded and closed disposal condition which contains the soiled product. Any operative, containment-closure mechanism may be employed. For example, the containment-closure mechanism can include an adhesive bond, a cohesive bond, a thermal bond, an ultrasonic bond, a snap fastener, a button fastener, a zipper, a drawstring system, an interengaging mechanical fastener, hook-and-loop fastener or the like, as well as combinations thereof.

Figure 5:
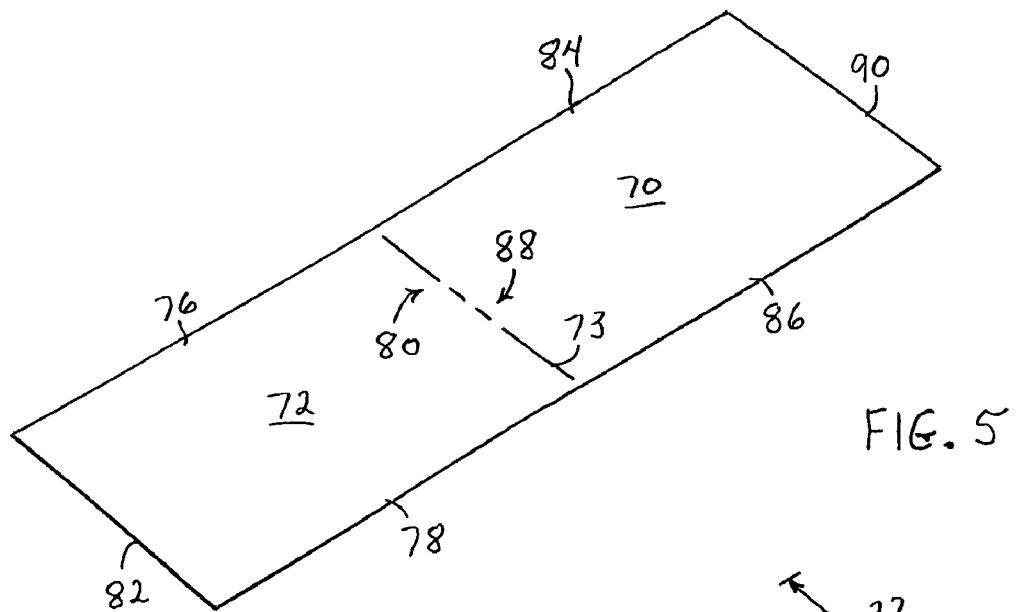
FIG. 5 shows a perspective view of a representative web component which is configured to provide a primary web portion and a supplemental web portion.
Figure 5A:
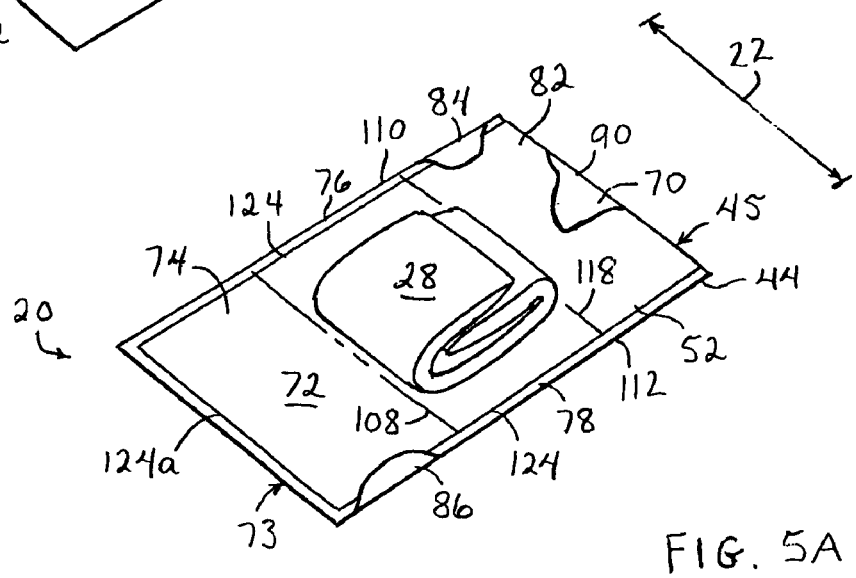
FIG. 5A representatively shows a perspective view of a folded product positioned on a partially cut-away composite web.
Figure 5B:
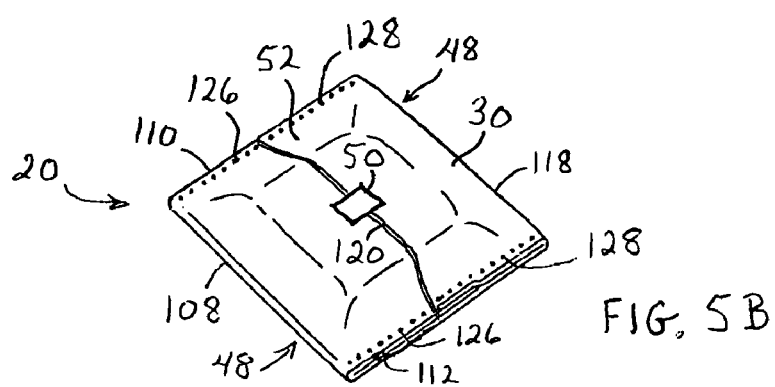
FIG. 5B shows a representative, perspective view of a folded product enclosed by a pouch formed from a composite web.
Figure 6:
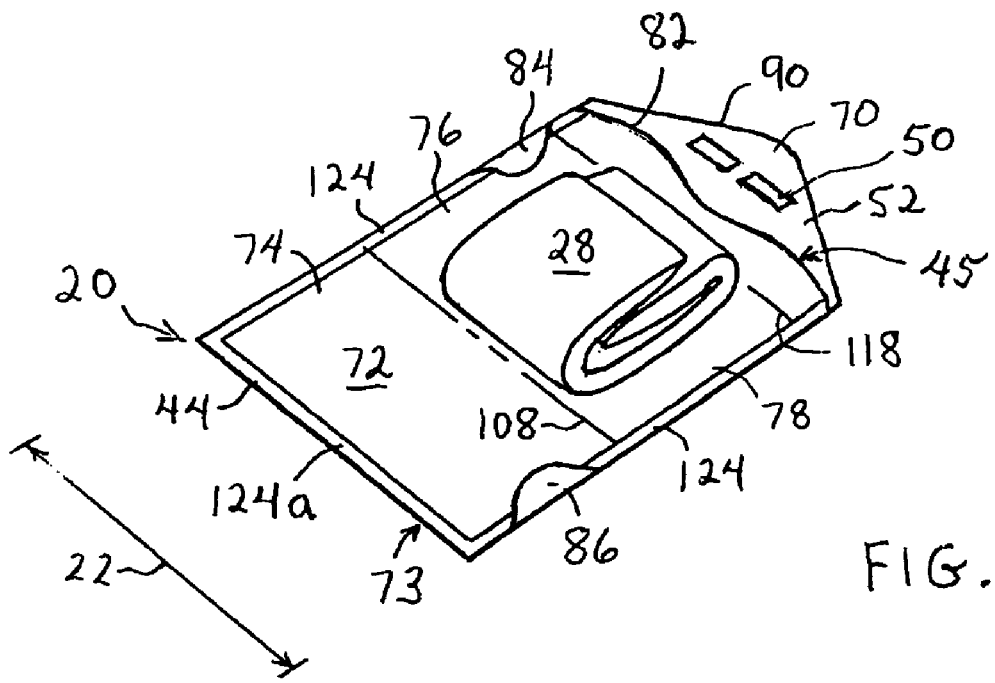
FIG. 6 representatively shows a partially cut-away, perspective view of a folded product positioned on another configuration of the composite web.
Figure 6A:
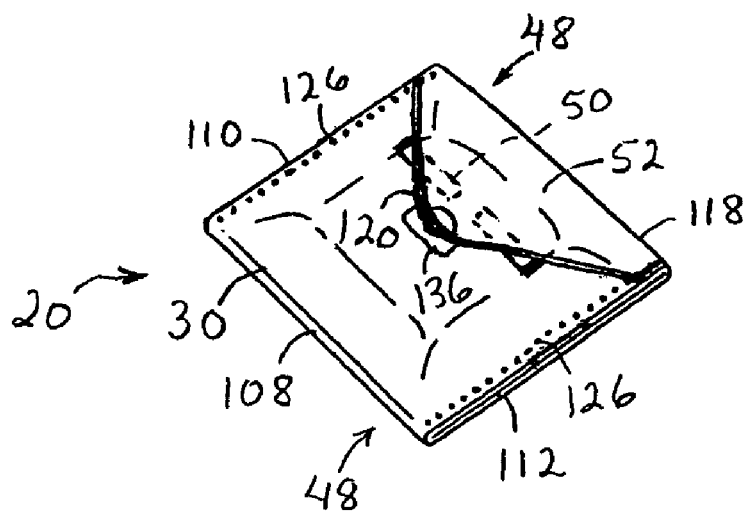
FIG. 6A shows a representative, perspective view of a folded product enclosed by a pouch formed from an alternative configuration of the composite web.

The article of the invention can have various alternative configurations. With reference to FIGS. 5-5A, for example, at least a portion of the front panel 32 and at least a portion of the back panel 34 can be provided by a primary web layer region 70. The article 20 can further include a supplemental web layer region 72 which is configured to overlie at least a portion of the primary web layer 70 to provide a composite web 74. As representatively shown, the supplemental web layer region 72 can be configured to overlie the entirety of the primary web layer region 70 to provide the composite web 74 (e.g. FIG. 5A). The supplemental web layer region 72 can alternatively be configured to overlie a portion, which is less than the entirety, of the primary web layer region 70 to provide the composite web 74 (e.g. FIG. 6). Accordingly, the supplemental web layer region can be configured to overlie at least a major portion of the primary web layer 70 to provide the composite web. The supplemental web layer region 72 may be a component that is provided separate from the primary web layer region 70. As representatively shown, the supplemental web layer region 72 and the primary web layer region 70 may alternatively be provided by a substantially unitary web component. The unitary web component may be folded or otherwise operatively turned along an appointed web-turn region 73 to form the composite web 74.

The primary web layer 70 can have a corresponding first side edge region 84, second side edge region 86, a first end region 88 and a second end region 90. The edge of the second end region 90 of the primary web layer may be substantially straight (e.g. FIG. 5A) and parallel to the article length 22. Alternatively, the edge of the second end region 90 may be slanted, jagged, curvilinear or the like, as well as combinations thereof (e.g. FIGS. 6 and 6A). The supplemental web layer 72 can have a corresponding first side edge region 76, second side edge region 78, a first end edge region 80 and a second end edge region 82. The edge of the second end region 82 of the supplemental web layer 72 may be substantially straight (e.g. FIG. 5A) and parallel to the article length 22. Alternatively, the edge of the second end region 90 may be slanted, jagged, curvilinear or the like, as well as combinations thereof. The first side-edge region 76 and second side-edge region 78 of the supplemental web layer 72 can be substantially permanently secured to a corresponding first side region 84 and second side region 86, respectively, of the primary web layer 70 with substantially permanent attachments 124 to form a disposal envelope or other disposal container 44. Where the primary web layer 70 and the supplemental web layer 72 are separately provided components, a base region of the primary web layer and a corresponding base region of the supplemental web layer can be affixed with an additional, substantially permanent attachment 124a, as may be needed to form the desired disposal container 44.

Accordingly, the disposal container 44 can have an appointed open-end region 45 which is generally positioned along the end edge regions 82 and 90 of the supplemental and primary web layers 72 and 70, respectively. The end edge regions 82 and 90 may be substantially unattached together or may be releasably attached, as desired. A soiled product can be placed into the disposal container by first separating apart the primary web layer 70 and the supplemental web layer 72 along the open-end region 45. Then, the soiled product can be inserted into the relatively large volume that can be readily generated between the spaced-apart portions of the primary web layer and supplemental web layer.

The composite web 74 can be operatively folded or otherwise turned about an appointed first turn-region 108 to thereby provide at least a first portion of the expansion section 48 of the article 20. A cooperating pair of companion portions of the first side region 110 of the composite web 74 can be releasably secured together with releasable attachments 126, and a cooperating pair of companion portions of a second side region 112 of the composite web 74 can be releasably attached together with additional releasable attachments 126, thereby holding at least a corresponding portion of the expansion section 48 in a substantially unexpanded, closed position. Additionally, the releasable attachments 126, along the first side region 110 and second side region 112, can help to at least partially form and maintain a desired pouch 30 which encloses the personal care product 28 in its fresh condition.

The composite web 74 can also include a flap section 52. The flap section of the composite web can be folded or otherwise operatively turned about an appointed, second turn-region 118 to further enclose the product 28 and to further form the intended pouch 30. Additionally, the folding or other turning of the flap section 52 about the turn-region 118 can thereby provide at least a second portion of the expansion section 48 of the article 20. The pouch closure mechanism 50 can then be employed to operatively and releasably hold the pouch 30 in a closed configuration which encloses the fresh product 28. In the various configurations of the invention, the pouch closure mechanism may, for example, include an adhesive bond, a cohesive bond, a thermal bond, an ultrasonic bond, a snap fastener, a button fastener, a zipper, a drawstring system, an interengaging mechanical fastener, hook-and-loop fastener or the like, as well as combinations thereof.

The pouch closure mechanism 50 can also help hold a corresponding portion of the expansion section 48 (e.g. the flap portion of the expansion section) in the desired, substantially unexpanded, closed position. As representatively shown, the pouch closure mechanism 50 can include one or more closure components that are operatively distributed along a free-edge region 120 of the flap section 52. Optionally or additionally, the pouch closure mechanism 50 can include a system or distribution of releasable attachments 128 that are positioned along one or more side-edge regions 122 of the flap section 52.

As representatively shown, the free-edge region 120 of the flap section 52 can include the appointed open-end region 45 of the container 44. It should be readily appreciated that the free-edge region 120 of the flap section 52 may alternatively include an opposite, closed-end region of the container 44. The terminal edge of the free-edge region 120 of the flap section 52 may be substantially parallel to the width 22 of the article (e.g. FIG. 5B), or may be nonparallel to the width 22 of the article (e.g. FIG. 6A). The pouch closure mechanism 50 may or may not be coterminous with the free-edge region of the flap section 52. Where the free-edge region of the flap section is non-coterminous with the article width, or where the terminal edge of the pouch closure mechanism is otherwise spaced away from the free edge of the flap, a portion of the free-edge region can remain loose and more readily grasped by the user to open the pouch 30.

The free-edge region 120 of the flap section 52 may optionally include an identification mechanism 136 (e.g. FIG. 6A) which can help to identify and locate the free-edge region for convenient grasping by the user. The identification mechanism can include an area of contrast that is readily perceptible by the user, and may, for example, include an operative region of contrasting tactile feel, contrasting color, contrasting pattern or the like, as well as combinations thereof. Additionally, the identification mechanism 136 can be positioned on an operative portion of the flap section 52, on a portion of the pouch 30 that is operatively adjacent the flap section 52, or combinations thereof.

In its various configurations and arrangements, the pouch closure mechanism 50 can be operatively released and opened to allow a convenient access and removal of the fresh product 28 from the pouch 30. Additionally, the release of the pouch closure mechanism 50 and the opening of the releasable attachments 126, 128 can allow a desired opening and activating of the expansion section 48. After a removal of the fresh product from the pouch and a disengagement of any employed releasable flap attachments 128, the turn-region 118 can be operatively straightened and moved to its open position. Additionally, the releasable pouch attachments 126 can be disengaged, and the turn-region 108 of the composite web 74 can be operatively straightened and moved to its open position. As a result, the expansion section 48 can be readily movable to the desired open, expanded position. The open positions of the turn-regions 108 and 118 can thereby provide an open position of the expansion section which is configured to provide the desired, increased disposal volume that can operatively contain the product 28 when the product is in its used and soiled condition.

The expanded pouch can provide a disposal container with an opening 130 that is wide enough to accept a used absorbent article that has been swollen with absorbed liquids. Additionally, the opened position of the expansion section can operatively reconfigure the pouch to provide a disposal container having an increased container volume that is significantly larger than the initial volume of the pouch when the pouch was arranged to hold the fresh product. The resulting container generated by the expanded pouch can have dimensions and size that are sufficient to provide a disposal volume that can operatively contain the product 28 when the product 28 has swollen to a size that significantly exceeds the size of the initial, fresh product. Accordingly, the disposal volume of the container provided by the expanded pouch can have dimensions and size that are sufficient to contain the used and soiled product for convenient disposal.

The turned condition of the turn-regions 108, 118 of the composite web 74 can be provided by any operative system or configuration. As representatively shown, the turn-region can include a single fold or single curl of the composite web 74. Alternatively, the turn-region can include a multi-folded or multi-curled configuration of the composite web 74.

Figures 7, 7A:
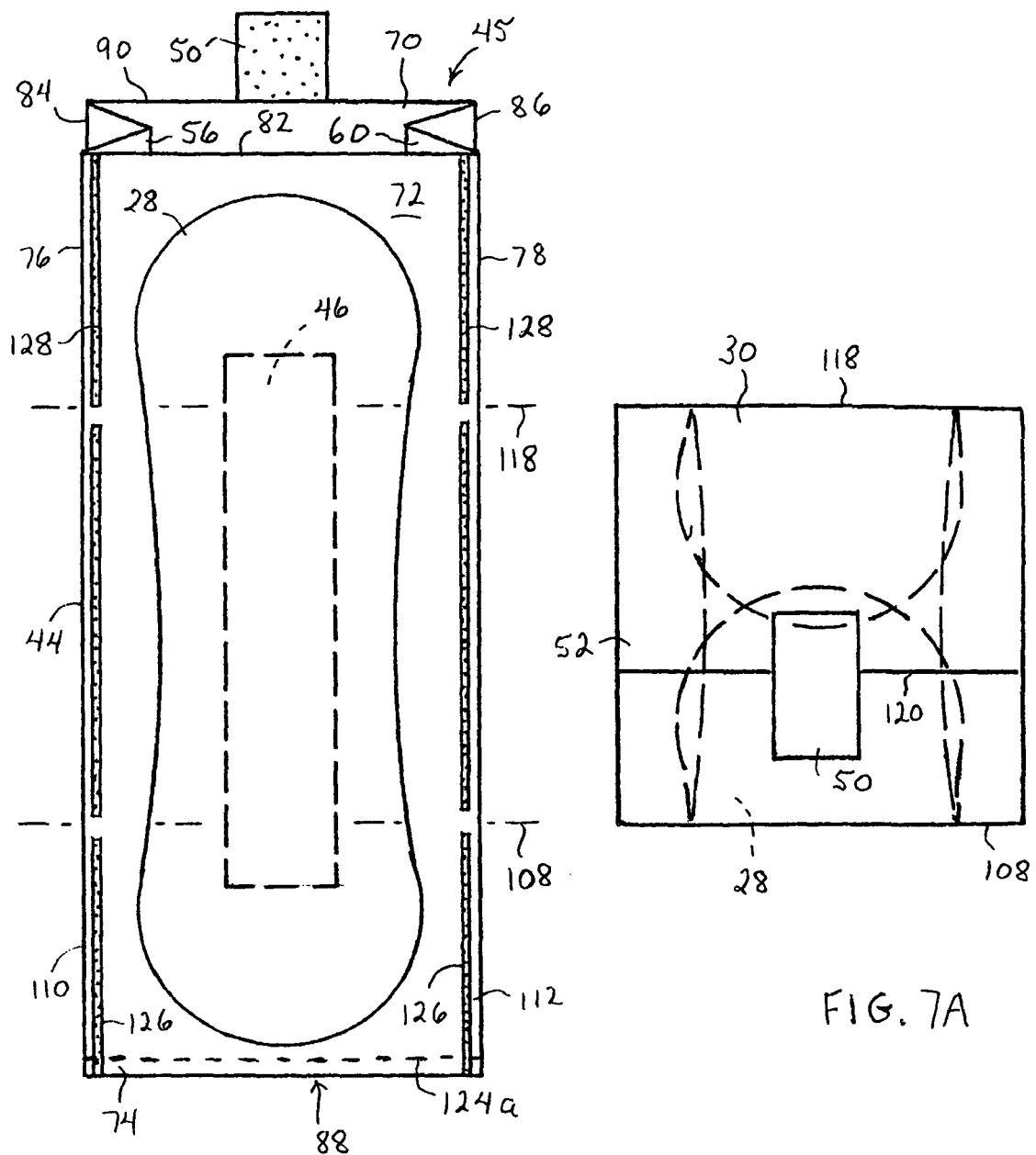
FIG. 7 shows a representative view of a substantially unfolded product placed on an unfolded composite web which includes a system of expandable gusset members.
FIG. 7A shows a representative view of a wrapped product after the combined product and associated composite web have both been folded together at the same time.

Other configurations of the article 20 can include any desired combinations of the various aspects and features of the invention. With reference to FIGS. 7-7A, for example, at least a portion of the front panel 32 and at least a portion of the back panel 34 can be provided by a primary web layer region 70. The article 20 can further include a supplemental web layer region 72 which is configured to overlie at least a portion of the primary web layer 70 to provide a composite web 74. As representatively shown, the supplemental web layer region 72 can be configured to overlie the entirety of the primary web layer region 70 to provide the composite web 74 (e.g. FIG. 5A). The supplemental web layer region 72 can alternatively be configured to overlie a portion, which is less than the entirety, of the primary web layer region 70 to provide the composite web 74 (e.g. FIG. 6). Accordingly, the supplemental web layer region can be configured to overlie at least a major portion of the primary web layer 70 to provide the composite web. The supplemental web layer region 72 may be a component that is provided separate from the primary web layer region 70. As representatively shown, the supplemental web layer region 72 and the primary web layer region 70 may alternatively be provided by a substantially unitary web component. The unitary web component may be folded or otherwise operatively turned along an appointed web-turn region 73 to form the composite web 74.

The primary web layer 70 can have a corresponding first side-edge region 84, second side-edge region 86, a first end region 88 and a second end region 90. The edge of the second end region 90 of the primary web layer may be substantially straight (e.g. FIG. 5A) and parallel to the article length 22. Alternatively, the edge of the second end region 90 may be slanted, jagged, curvilinear or the like, as well as combinations thereof (e.g. FIGS. 6 and 6A). The supplemental web layer 72 can have a corresponding first side edge region 76, second side edge region 78, a first end edge region 80 and a second end edge region 82. The edge of the second end region 82 of the supplemental web layer 72 may be substantially straight (e.g. FIG. 5A) and parallel to the article length 22. Alternatively, the edge of the second end region 90 may be slanted, jagged, curvilinear or the like, as well as combinations thereof.

The first side-edge region 76 and second side-edge region 78 of the supplemental web layer 72 can be operatively connected and secured to a corresponding first side region 84 and second side region 86, respectively, of the primary web layer 70. Additionally, the expansion section 48 of the composite web 74 and article can further include at least one gusset member 56. Desirably, the expansion section can include a cooperating pair of gusset members 56 and 60, and the gusset members can be positioned at corresponding, opposed side-edge regions of the primary and supplemental web layers (70, 72). As representatively shown, for example, the first gusset member 56 can be operatively interconnected between the first side region 84 of the primary web layer and the first side region 76 of the supplemental web layer, and the second gusset member 60 can be operatively interconnected between the second side region 86 of the primary web layer and the second side region 78 of the supplemental web layer to form the disposal envelope or other disposal container 44. An appointed base end region of the primary web layer and a corresponding base end region of the supplemental web layer can be operatively attached or otherwise operatively connected to form the desired disposal container 44. For example, the base end-regions can be operatively affixed with one or more additional, substantially permanent attachments 124a, as may be desired to form the disposal container.

Accordingly, the disposal container 44 can have an appointed open-end region 45 which is generally positioned along the end edges regions 82 and 90 of the supplemental and primary web layers 72 and 70, respectively. The end edge regions 82 and 90 may be substantially unattached together or may be releasably attached, as desired. A soiled product can be placed into the disposal container by separating apart the primary web layer 70 and the supplemental web layer 72 along the open-end region 45 and operatively expanding the gusset members (56, 60). Then, the soiled product can be inserted into the relatively large volume that can be readily generated between the spaced-apart portions of the primary web layer and supplemental web layer.

As previously disclosed, the product 28 may be folded prior to contacting the product with any portion of the pouch 30. An optional aspect of the invention can include a folding of the product 28 while the product is in contact with at least a selected portion of the pouch material. Accordingly, the pouch material and the product can be substantially simultaneously folded during a combined and coordinated operation. With reference to FIGS. 7 and 7A, the composite web 74 can be arranged with the expandable gusset members (56, 60) positioned and operatively held in a substantially flat, unexpanded condition, and a substantially unfolded product 28 can be laid or otherwise placed onto an appointed, cooperating portion of the composite web (e.g. onto the supplemental web layer 72). The product may or may not include the peel strip 42 (e.g. FIG. 3A). Where the product does not include the peel strip, a suitable release mechanism (e.g. an adhesive-release material) can be operatively attached to the surface of the composite web that is appointed to directly contact the selected garment-attachment mechanism (e.g. garment adhesive 46) that has been employed with the product 28.

The composite web 74 and the product 28 can both be operatively folded or otherwise turned about the appointed first turn-region 108 to begin the enclosure of the product in the appointed pouch. A cooperating pair of companion portions of the first side region 110 of the composite web 74 can be releasably secured together with releasable attachments 126, and a cooperating pair of companion portions of the second side region 112 of the composite web 74 can be releasably attached together with additional releasable attachments 126, thereby at least partially folding the product 28, and holding at least a corresponding portion of the expansion section 48 in a substantially unexpanded, closed position. Additionally, the releasable attachments 126, along the first side region 110 and second side region 112, can help to at least partially form and maintain a desired pouch 30 which encloses the personal care product 28 in its fresh condition.

The composite web 74 can also include the flap section 52, and at least a portion of the product 28 can overlie the flap section. The flap section of the composite web and any overlying portion of the product 28 can be folded or otherwise operatively turned about the appointed, second turn-region 118 to further enclose the product 28 and to further form the intended pouch 30. Additionally, the folding or other turning of the flap section 52 about the turn-region 118 can thereby provide at least another portion of the expansion section 48 of the article 20. The pouch closure mechanism 50 can then be employed to operatively and releasably hold the pouch 30 in a closed configuration which encloses the fresh product 28.

It should be readily appreciated that the construction material of any layer or web of the pouch 30, of the composite web 74 and/or of any gusset member (56, 60) can be provided by any suitable or desired material. For example, the material can be a polymer film, a nonwoven fabric, a woven fabric, a paper layer, a tissue layer or the like as well as laminates and other combinations thereof. The materials may be configured to be flexible, elastomeric, substantially nonelastomeric, rigid or semi-rigid, extensible, substantially non-extensible, or the like, as well as combinations thereof.

Examples of extensible materials are disclosed in U.S. Pat. No. 5,611,790, which is incorporated herein by reference. The extensible materials may be an intrinsically extensible material, such as a film or nonwoven made from a polyethylene/KRATON blend (e.g. EXXON film EXX-7). Alternatively, an initially inextensible material may be processed to render it operatively extensible by employing a post treatment, such as corrugating or ring rolling.

Even when the expanded pouch or disposal container has been sized and dimensioned to enclose a used, soiled product, presence of the garment attachment adhesive and the user's lack of dexterity may combine to inhibit the ready placement of the soiled product in the expanded pouch or disposal container. To address these situations, a particular aspect of the invention can include a mechanism to keep the soiled product in a closed configuration, and/or a deactivator mechanism for blocking, removing or otherwise operatively inhibiting the operation of the employed garment attachment mechanism (e.g. the garment adhesive). With the operative deactivation of the garment adhesive, a consumer can more easily insert a soiled product into an expanded pouch or disposal container.

After using an absorbent article, a consumer may typically roll or fold the product with the garment adhesive located on an outward-facing side of the rolled or folded product. In a particular feature, the flaps or wings 54 can be configured to operatively hold the product 28 in a closed or folded configuration when the product is in either its pre-use fresh configuration or post-use soiled configuration. Such configurations of the wings 54 are described in U.S. Pat. No. 5,478,336 and U.S. Pat. No. 5,358,499, which are incorporated herein by reference. To help compensate for the expanded volume of the soiled product the wings or flaps may be extensible. Suitable extensible materials and configurations of the wings are described in U.S. Pat. No. 5,611,790, which is incorporated herein by reference.

When attempting to insert the soiled product into a pouch or container for disposal, the garment adhesive can undesirably engage and attach to the pouch or container. This can make it difficult to hide the used product in a trash receptacle. To help alleviate this difficulty, the garment adhesive can be deactivated or otherwise inhibited after the product has been soiled, and prior to or while the soiled product is being placed into the pouch or bag for disposal. Additionally or alternatively, the inside of the disposal pouch or disposal container can be treated with an operative release agent or other low-adhesion material.

The article 20 can, for example, include an operative layer of a release material or other low-adhesion material, which is distributed along an exposed inner-most surface 116 (e.g. FIG. 4A) of at least one of the front panel region 32 and back panel region 34. In a desired arrangement, an exposed innermost surface 116 of each of the front and back panel regions 32, 34 can include an operative layer of the low-adhesion material. Where the article includes gusset members 56, 60, the innermost surfaces of the gusset members may also include an operative layer or other distribution of the low-adhesion material. Where the article includes a primary web layer 70 and a supplemental web layer 72 configured to provide a disposal container, adjacent facing-surfaces of the primary web layer 70 and the supplemental web layer 72 can include an operative layer or other distribution of the low-adhesion material. Accordingly, the innermost surfaces of the appointed disposal container can include an operative layer or other distribution of the low-adhesion material.

The low-adhesion material can, for example, include a silicone release material, and can be distributed to operatively line the inside of the disposal pouch or disposal container, so that if the garment adhesive were to touch the pouch or container material, the garment adhesive would not readily adhere. The inside of the disposal pouch or disposal container can alternatively be treated with a powder. When the powder contacts the adhesive, the adhesive would lose its tackiness.

Another mechanism or system to inactivate the garment adhesive can include an adhesive that is selectively active. The adhesive can be arranged to be tacky or activate when product 28 is being placed in the associated undergarment, but can be configured to be non-tacky or inactivate when the product 28 is being placed into the expanded pouch for disposal. The resulting "deactivatable" adhesive is an adhesive which loses at least a significant portion of its tack or adhesion strength (i.e. deactivated) when certain action is performed by the user or caregiver or when the adhesive is exposed to certain conditions. For example, an adhesive may be deactivated when the caregiver detaches the adhesive and then avoids applying a particularly high pressure needed to activate an adhesive bond. In another example, the adhesive may be deactivated when the article is subject to an environmental condition (e.g. ambient air, body temperature, a cooling device, and or evaporative process) which cools the adhesive below a critical temperature. Such deactivatable adhesive systems include pressure-activated adhesive systems, temperature-activated adhesive systems or the like.

Pressure-activated adhesive systems are described in U.S. Pat. No. 4,336,804; U.S. Pat. No. 4,337,772; U.S. Pat. No. 4,376,772; U.S. Pat. No. 4,376,440; U.S. Pat. No. 4,475,913; U.S. Pat. No. 4,959,265; and U.S. Pat. No. 5,662,758; the disclosures of which are incorporated herein by reference. An example of a pressure-activated system is a backsheet that has thermoformed protrusions that extend between a grid of pressure sensitive adhesive. The protrusions prevent adhesion of the backsheet to the pouch. The protrusions can be configured to locally collapse when the protrusions are subjected to preselected, high level of applied pressure, and the collapse can enable the adhesive to contact and stick to the undergarment. When placing the soiled product into the expanded pouch, however, the applied pressure will be insufficient to collapse the protrusions.

Temperature-activated adhesive systems are described in U.S. Pat. No. 6,572,600, which is incorporated herein by reference. A particular example of a temperature-activated system can include an adhesive that is tacky at body temperature, but loses a significant portion of its tackiness when subjected to ambient, room temperature. Such adhesives are described in U.S. Pat. No. 5,387,450, which is incorporated herein by reference.

Figure 8A:
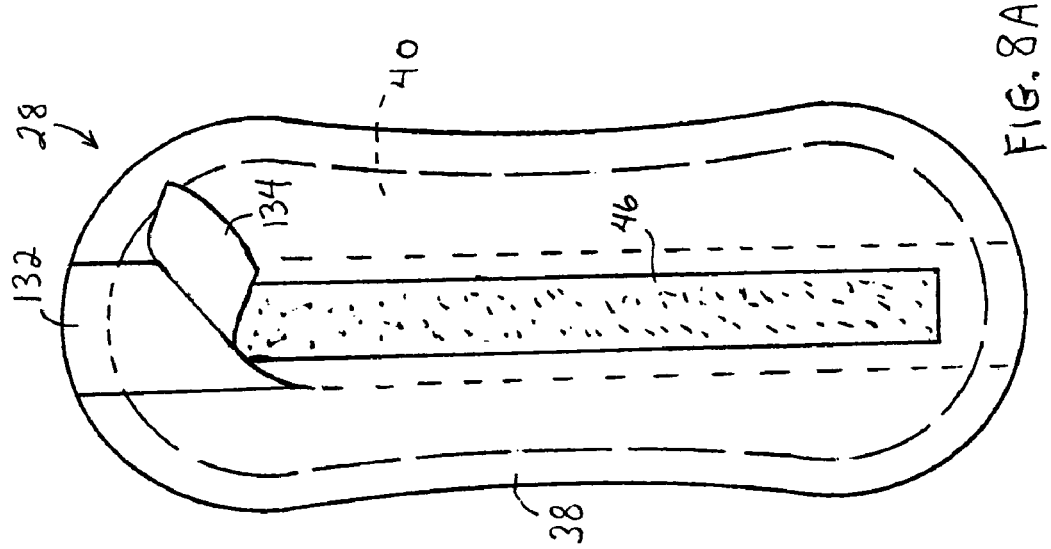
FIG. 8A shows the article of FIG. 8 in which a strip of an outer backsheet layer can be removed to deactivate the garment adhesive.
Figure 8:
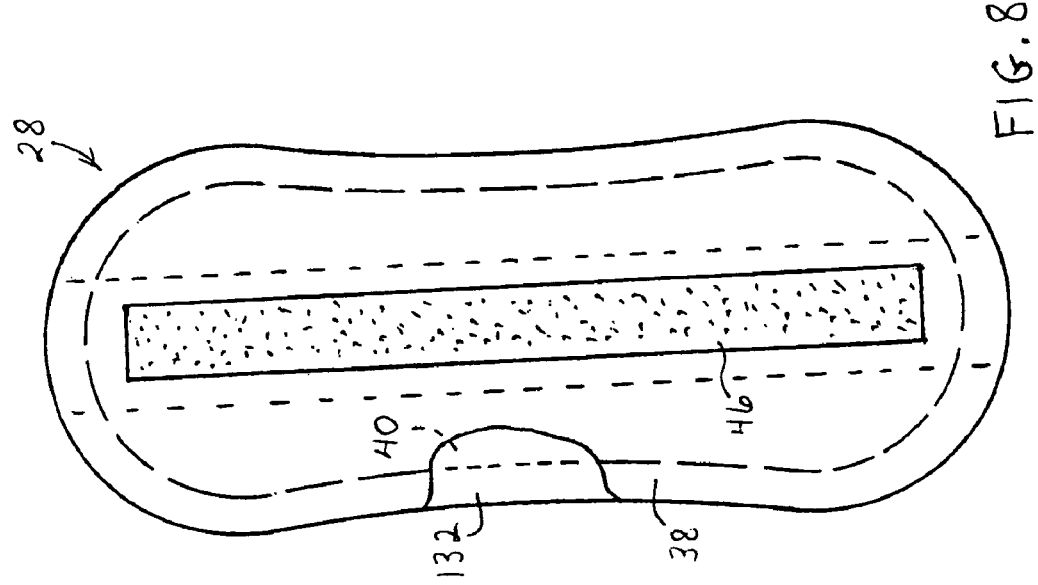
FIG. 8 shows a plan view of a representative product which includes an inner backsheet layer, and a system for deactivating a garment adhesive.

A further mechanism or system to deactivate the garment adhesive after the article has been soiled can include a mechanism or system for removing the garment adhesive from the product 28 prior to inserting the soiled product into the appointed disposal pouch or container: With reference to FIGS. 8-8A, for example, a product may be configured to include two or more backsheet layers to provide an outer backsheet layer 38, and at least one inner backsheet layer 132. The inner backsheet layer could be operatively liquid-impermeable to effectively contain the absorbed liquid, and the outer backsheet layer could be configured to carry the garment adhesive. To deactivate the garment adhesive, the entire outer backsheet layer or at least an operative portion of the outer backsheet layer can be removed from the product. For example, the outer backsheet layer could be perforated, such that a strip 134 of the outer backsheet layer can be removed from the product. The outer backsheet layer or the strip of the outer backsheet layer could be removed after the absorbent article has been removed from the user's underwear. Optionally, the outer backsheet layer or the appointed strip of the outer backsheet layer can be removed from the article as the user removes the product from the user's undergarment. In this case, the user would remove the product, and then remove the adhesive-carrying strip 134 of the outer backsheet layer from the underwear.

In any of the configurations involving the removal of the garment adhesive, the outer backsheet layer having the garment adhesive can be employed to assist in the disposal of the soiled product. For example, the outer backsheet material, once removed from an absorbent article, may be employed to hold or secure the soiled product in a folded or rolled configuration. The folded or rolled product could then be inserted into a desired disposal pouch or disposal container without incurring undesired attachments between the soiled product and the appointed disposal pouch or container.

The invention can be configured to increase the discretion of discarding a used product. This can be accomplished by having a disposal pouch or disposal container, which has been configured to audio-visually camouflage the article with regard to sound and sight. Increased discretion can also be obtained by having the disposal means cover, mask, or contain any odor or malodor emanating from a used product. Ideally, the disposal means would incorporate both audio-visual and olfactory masking.

In particular arrangements, the disposal pouch or disposal container can be made of a material that provides an effective barrier to fluids and odor. Optionally, the pouch or container material may include an absorbent material. In other arrangements, the article of the invention can provide a disposal pouch or disposal container, which has been configured to visually mask or camouflage the soiled product. The material of the disposal pouch or disposal container can be configured to be sufficiently opaque, such that the soiled product cannot be seen through the pouch or container material. For example, opaque nano-particles or other light blocking or absorbing mechanisms or chemistries can be used. The pouch or container material can also be printed such that the pouch or container material matches items commonly found in trash receptacles. For example, the pouch or container material could be printed to resemble a used, crinkled facial tissue.

The pouch or container material may also contain an operative amount of an odor control element that can effectively absorb or mask odor. Optionally, the odor control agent or element may be configured to provide a visual barrier. It should also be appreciated that the odor control element can be provided in any operative form. For example, the odor control element or agent can include an anthraquinone material (e.g. an anthraquinone dye) and/or an activated carbon (e.g. a printed design or other array of activated carbon). The pouch or container material could itself contain the odor control agent, or the user could apply the odor control agent. For example, a bottle or other quantity of an odor control agent could be attached to the article provided to a consumer. The consumer could then add the odor control agent to the used and soiled product. Where the product 30 includes inner and outer backsheet layers, the employed inner and outer backsheet layers may be held together by a backsheet adhesive, and the backsheet adhesive may contain an odor control agent or a fragrance. When the outer cover is removed from the inner cover, the odor control agent or fragrance could then become exposed and activated.

The odor control element can optionally be activated during the process of expanding or opening the gusset structure. A mechanism to activate an odor control element by the separation of layers like those found in the unopened gusset members (58, 60) are described in U.S. Pat. No. 4,186,743, which is incorporated by reference. The odor control element can be encapsulated in a selected material, and this material can be broken by the process of expanding or opening the gusset structures. This encapsulating material can be microcapsules or some other form of encapsulation, as described in U.S. Patent Application Publication 2004/0266302, which is incorporated-herein by reference. The employed odor control element may include a fragrance to help cover up any malodor.

The individual personal care product 28 can be grouped with several other personal care products and the grouped personal care products are placed in a retail container or package (not shown). It may also be desirable to group several absorbent products 28 in a conveniently sized sub-pack for daily use. Further, it may be desirable to group products of different types, different sizes and/or or of different absorbent capacities together in a single package. A suitable package can be provided by any operative, soft or hard packaging material. Soft packaging includes flexible envelopes and articles made of sheet plastic and/or paper. Hard packaging includes generally less flexible articles made of plastic (e.g., tubs and buckets), metal or cardboard, as well as combinations thereof. In a particular aspect, the package can be reclosable.

In view of the present disclosure, it is readily apparent that the several objects of the invention are achieved and other advantageous results are attained. Since various changes and modifications can be made in the above constructions without departing from the scope of the invention, it is intended that all matter contained in the above description or shown in the accompanying drawings shall be interpreted as illustrative and not in a limiting sense.

The invention claimed is:

1. An article, having a longitudinal length, a width and a thickness, the article comprising: a fresh personal care product in a substantially unsoiled condition; and a pouch which operatively encloses the fresh product; the pouch including
a front panel;
a back panel which is operatively connected to the front panel;
a first gusset member which is operatively interconnected between a first end edge portion of the front panel and a first end edge portion of the back panel, the first gusset member having at least one longitudinal fold-line therein;
a second gusset member which is operatively interconnected between a second end edge portion of the front panel and a second end edge portion of the back panel, the second gusset member having at least one longitudinal fold-line therein;
a pouch closure mechanism which operatively holds the pouch in a closed configuration which encloses the fresh product; and
a pouch opening mechanism;
wherein
the pouch closure mechanism includes
a first attachment between a first side-portion of the front panel and a first side-portion of the back panel;
a second attachment between a second side-portion of the front panel and a second side-portion of the back panel;
the pouch opening mechanism includes a frangible line of weakness positioned along the first attachment;
the first gusset member and second gusset member are each operatively held in a substantially unexpanded, folded, closed position when the fresh product is enclosed in the pouch;
the first gusset member and second gusset member are each movable to an open position after a removal of the product from the pouch;
the open positions of the first gusset member and second gusset member are configured to provide an expanded disposal volume which can operatively contain the product when the product is in a used and soiled condition.

2. An article as recited in claim 1, wherein
the first gusset member is constructed with an extensible material.

3. An article as recited in claim 1, wherein
the product has a total saturated retention capacity of at least about 100 grams of 0.9 wt % saline; and
the open position of the expansion section is configured to provide an expanded disposal volume which can operatively contain the product after the product has absorbed 20% of the total saturated retention capacity of the product.

4. An article as recited in claim 1, wherein the pouch-opening mechanism operatively allows a removal of the fresh product from the pouch.

5. An article as recited in claim 1, the pouch further comprising a pouch volume that operatively encloses the fresh product, wherein the disposal volume is greater than the pouch volume.

6. An article as recited in claim 1, further including a containment-closure mechanism which is configured to hold the pouch in an expanded and closed disposal condition which contains the soiled product.

7. An article as recited in claim 1, wherein the personal care product includes a liquid-permeable topsheet layer, a backsheet layer, and an absorbent body which is operatively sandwiched and held between the topsheet layer and backsheet layer.

8. An article as recited in claim 1, wherein the personal care product has been separately folded prior to engagement with the pouch.

9. An article as recited in claim 1 wherein
- the first attachment between the first side-portion of the front panel and the first side-portion of the back panel is a first bonded attachment; and
- the second attachment between the second side-portion of the front panel and the second side-portion of the back panel is a second bonded attachment.

10. An article as recited in claim 1 further comprising a pouch-opening mechanism which operatively allows a removal of the fresh article from the pouch; the pouch-opening mechanism including a frangible line of weakness which is located relatively inboard from said first attachment between the first end-region of the front panel and the first end-region of the back panel.

11. An article as recited in claim 1, wherein
- at least a portion of the front panel and at least a portion of the back panel are provided by a primary web layer;
- the article further includes a supplemental web layer which is configured to overlie at least a portion of the primary web layer to provide a composite web;
- a first side-edge region, a second side-edge region and a first end-edge region of the supplemental web layer are substantially permanently attached to a corresponding first side-edge region, second side-edge region and a first end-edge region of the primary web layer to form a disposal envelope;
- the composite web is operatively turned about an appointed turn-region to thereby provide at least a portion of the expansion section of the article;
- a pair of companion portions of a first side region of the composite web are releasably attached together, and a pair of companion portions of a second side region of the composite web are releasably attached together, thereby holding the expansion section in a substantially unexpanded, closed position;
- the personal care product has been separately folded prior to engagement with the front and back panels of the pouch; and
- the pouch closure mechanism includes a flap section of the composite web, and a closure attachment mechanism that releasably holds the flap in a closed position.

12. An article as recited in claim 11, wherein an operative layer of low-adhesion material is distributed along adjacent facing-surfaces of the primary web layer and supplemental web layer.

13. An article as recited in claim 1, wherein an operative layer of low-adhesion material is distributed along an exposed, inner-most surface of at least one of said front panel and back panel.

14. An article as recited in claim 1, wherein the personal care product includes
- a backsheet; a garment adhesive disposed on the garment-side of the backsheet; and a deactivator mechanism to operatively inhibit the garment adhesive when the personal care product is soiled and being placed for disposal.

15. An article as recited in claim 1, wherein the pouch includes a pouch material which has been configured to provide visual masking.

\* \* \* \* \*